US010893685B2

(12) United States Patent
Hotta et al.

(10) Patent No.: US 10,893,685 B2
(45) Date of Patent: Jan. 19, 2021

(54) CHLOROGENIC ACID-CONTAINING COMPOSITION MANUFACTURING METHOD

(71) Applicant: KAO CORPORATION, Tokyo (JP)

(72) Inventors: Yusuke Hotta, Kashima (JP); Yukiteru Sugiyama, Narita (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/345,188

(22) PCT Filed: Sep. 28, 2017

(86) PCT No.: PCT/JP2017/035266
§ 371 (c)(1),
(2) Date: Apr. 25, 2019

(87) PCT Pub. No.: WO2018/079177
PCT Pub. Date: May 3, 2018

(65) Prior Publication Data
US 2019/0281856 A1  Sep. 19, 2019

(30) Foreign Application Priority Data
Oct. 26, 2016  (JP) .................................. 2016-209197

(51) Int. Cl.
*A23F 5/26* (2006.01)
*A23L 33/105* (2016.01)
*B01D 11/02* (2006.01)
*C07C 67/58* (2006.01)
*C07C 67/48* (2006.01)
*C07C 69/732* (2006.01)

(52) U.S. Cl.
CPC .............. *A23F 5/26* (2013.01); *A23L 33/105* (2016.08); *B01D 11/0288* (2013.01); *C07C 67/48* (2013.01); *C07C 67/58* (2013.01); *C07C 69/732* (2013.01); *A23V 2002/00* (2013.01)

(58) Field of Classification Search
CPC ..... A23F 5/26; A23L 33/105; B01D 11/0288; A23V 2002/00
See application file for complete search history.

(56) References Cited

U.S. PATENT DOCUMENTS

| 4,048,345 | A | 9/1977 | Katz |
| 5,702,747 | A | 12/1997 | Sipos et al. |
| 9,029,588 | B2 | 5/2015 | Yamawaki et al. |
| 9,034,410 | B2 * | 5/2015 | Vella .......................... A23F 5/02 426/595 |
| 2006/0210689 | A1 | 9/2006 | Velissariou et al. |
| 2008/0044539 | A1 * | 2/2008 | Perlman ................ A23L 3/3481 426/542 |
| 2009/0092736 | A1 | 4/2009 | Koyama et al. |
| 2012/0251678 | A1 * | 10/2012 | Leloup ...................... A23F 5/02 426/112 |
| 2013/0131165 | A1 | 5/2013 | Sugiyama et al. |
| 2013/0230608 | A1 * | 9/2013 | Silber ....................... A23F 5/02 424/725 |
| 2014/0271988 | A1 | 9/2014 | Robinson et al. |
| 2017/0013857 | A1 | 1/2017 | Ozato |
| 2018/0160696 | A1 | 6/2018 | Ozato et al. |

FOREIGN PATENT DOCUMENTS

| EP | 0916267 | * | 5/1999 |
| EP | 2592064 A1 | | 5/2013 |
| EP | 2644036 A1 | | 10/2013 |
| GB | 1488340 A | | 10/1977 |
| JP | 2006-104070 A | | 4/2006 |
| JP | 2006-174746 A | | 7/2006 |
| JP | 2008-31150 A | | 2/2008 |
| JP | 2008-266144 A | | 11/2008 |
| JP | 2010-178664 A | | 8/2010 |
| JP | 2011-182749 A | | 9/2011 |
| JP | 2012-31165 A | | 2/2012 |
| JP | 2013-138631 A | | 7/2013 |
| JP | 2015-142565 A | | 8/2015 |
| JP | 2016-106627 A | | 6/2016 |
| JP | 6389940 B2 | | 9/2018 |
| JP | 2019-99 A | | 1/2019 |
| WO | WO 2007/122796 A1 | | 11/2007 |
| WO | WO 2012/005293 A1 | | 1/2012 |
| WO | WO 2014/155746 A1 | | 10/2014 |
| WO | WO 2015/093522 A1 | | 6/2015 |

(Continued)

OTHER PUBLICATIONS

English Translation for JP2011-182749 published Sep. 2011.*

(Continued)

*Primary Examiner* — Anthony J Weier

(74) *Attorney, Agent, or Firm* — Birch, Stewart, Kolasch & Birch, LLP

(57) ABSTRACT

Provided is a method of producing a chlorogenic acid-containing composition, including a step of subjecting coffee beans to column extraction using an aqueous solvent, in which the coffee beans include at least one selected from the group consisting of green coffee beans, decaffeinated green coffee beans, roasted coffee beans having an L value of 40 or more, and decaffeinated roasted coffee beans having an L value of 25 or more, and include at least one selected from the group consisting of unground coffee beans and ground coffee beans having an average particle size of 2.0 mm or more.

13 Claims, No Drawings

(56) References Cited

FOREIGN PATENT DOCUMENTS

WO    WO 2016/031625 A1    3/2016

OTHER PUBLICATIONS

International Search Report, dated Jan. 9, 2018, for International Application No. PCT/JP2017/035267, with an English translation.
International Search Report, dated Jan. 9, 2018, for International Application No. PCT/JP2017/035268, with an English translation.
Japanese Office Action, dated Apr. 6, 2018, for Japanese Application No. 2017-188160 with an English machine translation.
SUGI Blog, Sep. 6, 2014, retrived on Dec. 20, 2017, (https://ameblo.jp/sugichan0826/entry-11920899630.html) non-official translation (An Look at the ATAGO BRIX/TDS Scale), total of 7 pages.
International Search Report for PCT/JP2017/035266 (PCT/ISA/210) dated Jan. 9, 2018.
U.S. Appl. No. 16/345,118, filed Apr. 25, 2019.
U.S. Appl. No. 15/345,194, filed Apr. 25, 2019.
U.S Office Action, dated Dec. 4, 2019, for U.S. Appl. No. 16/345,118.
Author Unknown, "Carbohydrates in Coffee", URL: https:www.coffeechemistry.com/chemistry/carbohydrates/carbohydrates-in-coffee, XP055676898, Apr. 23, 2015, 5 pages.
Extended European Search Report, dated Mar. 23, 2020, for European Application No. 17863734.4.
Extended European Search Report, dated Mar. 25, 2020, for European Application No. 17865450.5.
Extended European Search Report dated Jun. 9, 2020, for European Application No. 17864962.0.

\* cited by examiner

CHLOROGENIC ACID-CONTAINING COMPOSITION MANUFACTURING METHOD

FIELD OF THE INVENTION

The present invention relates to a method of producing a chlorogenic acid-containing composition.

BACKGROUND OF THE INVENTION

As materials having bioactive functions, there have been proposed a variety of materials. For example, there are given polyphenols as those having bioactive functions, such as an antioxidative effect, an antihypertensive effect, and a hepatic function-improving effect. A chlorogenic acid, which is one of the polyphenols, has been reported to have a high antihypertensive effect, and is expected to find applications in supplements and food and beverage.

As a material containing a large amount of the chlorogenic acid, there are given coffee beans. A chlorogenic acid-containing composition obtained by extraction from the coffee beans has been conventionally investigated with regard to, for example, an increase in recovery rate of the chlorogenic acid, a reduction in impurities, such as caffeine, an improvement in taste and flavor, and an improvement in color. For example, as a technology useful for production of a chlorogenic acid-containing beverage in which occurrence of turbidity is reduced even in an acidic region, there is a proposal of a method involving bringing a chlorogenic acid-containing composition in a state of being dispersed or dissolved in a mixed solvent of an organic solvent and water into contact with a specific adsorbent, removing precipitates, then controlling the concentration of the chlorogenic acid and pH to specific ranges to further form precipitates, and performing solid-liquid separation (Patent Document 1).

(Patent Document 1) JP-A-2012-31165

SUMMARY OF THE INVENTION

The present invention provides a method of producing a chlorogenic acid-containing composition, including a step of subjecting coffee beans to column extraction using an aqueous solvent, in which the coffee beans comprise at least one selected from the group consisting of green coffee beans, decaffeinated green coffee beans, roasted coffee beans having an L value of 40 or more, and decaffeinated roasted coffee beans having an L value of 25 or more, and include at least one selected from the group consisting of unground coffee beans and ground coffee beans having an average particle size of 2.0 mm or more.

DETAILED DESCRIPTION OF THE INVENTION

The method described in Patent Document 1 is effective for reducing turbidity that occurs specifically in an acidic region when the concentration of a chlorogenic acid is diluted to an optimum concentration as a beverage. However, the method involves complicated production steps, and hence there is a demand for a simpler method.

The present invention relates to a method of producing a chlorogenic acid-containing composition that hardly causes turbidity even when the concentration of a chlorogenic acid is diluted to an optimum concentration as a beverage to provide an acidic beverage.

The inventors of the present invention made various investigations. As a result of investigations, they found that the above-mentioned problem can be solved by using coffee beans having specific properties and subjecting the coffee beans to column extraction with an aqueous solvent.

According to the present invention, a chlorogenic acid-containing composition that hardly causes turbidity even when the concentration of a chlorogenic acid is diluted to an optimum concentration as a beverage to provide an acidic beverage can be produced by a simple operation while the chlorogenic acid is recovered with a good yield.

Hereinafter, a method of producing a chlorogenic acid-containing composition of the present invention is described. The term "chlorogenic acid" as used herein is a collective term for monocaffeoylquinic acids including 3-caffeoylquinic acid, 4-caffeoylquinic acid, and 5-caffeoylquinic acid, and monoferuloylquinic acids including 3-feruloylquinic acid, 4-feruloylquinic acid, and 5-feruloylquinic acid. The content of the chlorogenic acid is defined based on the total amount of the six kinds of chlorogenic acids.

[Coffee Beans]

Coffee beans to be used are at least one selected from the group consisting of green coffee beans, decaffeinated green coffee beans, roasted coffee beans having an L value of 40 or more, and decaffeinated roasted coffee beans having an L value of 25 or more. As used herein, the term "decaffeinated green coffee beans" refers to coffee beans obtained by subjecting green coffee beans to decaffeination treatment, the term "roasted coffee beans having an L value of 40 or more" refers to coffee beans obtained by subjecting green coffee beans to roasting treatment so as to have an L value of 40 or more, and the term "decaffeinated roasted coffee beans having an L value of 25 or more" refers to coffee beans obtained by subjecting decaffeinated green coffee beans to roasting treatment so as to have an L value of 25 or more. Of those, as the coffee beans, green coffee beans are preferred from the standpoint of the content of the chlorogenic acid.

The bean species of the coffee beans may be, for example, any one of *Arabica*, *Robusta*, *Liberica*, and *Arabusta*. In addition, the producing region of the coffee beans is not particularly limited, and examples thereof include Brazil, Colombia, Tanzania, Mocha, Kilimanjaro, Mandheling, Blue Mountain, Guatemala, and Vietnam.

As a method of subjecting the green coffee beans to the decaffeination treatment, a known method may be adopted, and examples thereof may include a Swiss Water method, a supercritical carbon dioxide extraction method, and an organic solvent extraction method. Of those, a Swiss Water method or a supercritical carbon dioxide extraction method is preferred from the viewpoint of a reduction in turbidity.

The roasted coffee beans have an L value of 40 or more, and the L value is preferably 45 or more, more preferably 53 or more, even more preferably 55 or more, from the standpoint of the content of the chlorogenic acid, and is preferably less than 65, more preferably 60 or less, even more preferably 58 or less, from the viewpoint of taste and flavor. The L value of the roasted coffee beans falls within the range of preferably from 40 or more to less than 65, more preferably from 45 or more to less than 65, more preferably from 53 or more to less than 65, more preferably from 55 to 60, even more preferably from 55 to 58.

Meanwhile, the decaffeinated roasted coffee beans have an L value of 25 or more, and the L value is preferably 30 or more, more preferably 33 or more, from the standpoint of the content of the chlorogenic acid, and is preferably less than 50, more preferably 45 or less, even more preferably 40 or less, from the viewpoint of taste and flavor. The L value of the roasted coffee beans falls within the range of preferably from 25 or more to less than 50, more preferably from 30 to 45, even more preferably from 33 to 40. The term "L value" as used herein with regard to the roasted coffee beans or the decaffeinated roasted coffee beans refers to a value as determined by measuring the lightness of the roasted coffee beans with a colorimeter under the assumption that black has an L value of 0 and white has an L value of 100. The roasted coffee beans to be subjected to the measurement are ground to an average particle size of 0.3 mm.

The roasted coffee beans may be obtained by roasting green coffee beans, or may be a commercially available product. A method for the roasting is not particularly limited, and a known method may be appropriately selected. For example, a roasting temperature is preferably from 180° C. to 300° C., more preferably from 190° C. to 280° C., even more preferably from 200° C. to 280° C., and a heating time may be appropriately set so that a desired degree of roasting may be obtained. In addition, as a roaster, for example, a roaster for roasting beans kept unmoved, a roaster for roasting beans while transferring the beans, or a roaster for roasting beans while stirring the beans may be used. Specific examples thereof include a shelf dryer, a conveyer dryer, a rotary-drum dryer, and a rotary V-type dryer. As a heating system, there are given, for example, a direct heating system, a hot-air system, a half-hot air system, a far-infrared ray system, an infrared ray system, a microwave system, and a superheated steam system. Also in the case of the decaffeinated roasted coffee beans, roasting may be performed by a method similar to that for the roasted coffee beans described above, and a commercially available product may be used.

In addition, with regard to their particle size, the coffee beans may be unground (whole) coffee beans, ground coffee beans, or a mixture thereof. However, in the case of the ground coffee beans, ones having an average particle size of 2.0 mm or more are used. Of those, unground (whole) coffee beans are preferred from the viewpoint of a reduction in turbidity. The term "average particle size" as used herein with regard to the ground coffee beans refers to one measured by a measurement method described in Examples to be described later.

The average particle size of the ground coffee beans is preferably 2.5 mm or more, more preferably 3.5 mm or more, more preferably 4.5 mm or more, more preferably 5.5 mm or more, even more preferably 6.1 mm or more, from the viewpoint of a reduction in turbidity, and is preferably 7.5 mm or less, more preferably 7.0 mm or less, even more preferably 6.5 mm or less, from the viewpoint of a yield. Such average particle size falls within the range of preferably from 2.5 mm to 7.5 mm, more preferably from 3.5 mm to 7.0 mm, more preferably from 4.5 mm to 6.5 mm, more preferably from 5.5 mm to 6.5 mm, even more preferably from 6.1 mm to 6.5 mm.

A method of grinding the coffee beans is not particularly limited, and a known method and apparatus may be used. Examples of the grinding apparatus may include a cutter mill, a hammer mill, a jet mill, an impact mill, and a Wiley mill. Examples of the cutter mill include a roll grinder, a flat cutter, a conical cutter, and a grade grinder.

In addition, the ground coffee beans may be classified so as to have an average particle size in the above-mentioned range through the use of, for example, a Tyler standard sieve, an ASTM standard sieve, or a JIS standard sieve.

The coffee beans may be used alone or in combination thereof. When two or more kinds of coffee beans are used, not only coffee beans different in bean species or producing region, but also coffee beans different in degree of roasting or particle size may be appropriately selected and used in any combination. When coffee beans different in degree of roasting are used, the coffee beans are preferably used in such an appropriate combination that the average of their L values falls within the above-mentioned range. The average of the L values is determined as a sum of values each obtained by multiplying an L value of roasted coffee beans by a content mass ratio of the roasted coffee beans.

In addition, in the present invention, steamed coffee beans may be used as the coffee beans from the viewpoint of the yield of the chlorogenic acid. In the case of using steamed ground coffee beans as the coffee beans, ground coffee beans may be subjected to steam treatment, or whole ground coffee beans may be subjected to steam treatment before being ground.

As a method for the treatment, there may be given, for example, a batch method involving placing coffee beans in a pressure vessel, then supplying steam into the vessel, sealing the vessel, and keeping a high-temperature and high-pressure state for a certain period of time. In addition, there may also be adopted a continuous method involving placing coffee beans in a pressure vessel comprising a steam supply path and a steam discharge path, and then continuously performing the following operation for a certain period of time: steam is supplied through the steam supply path, and the steam is discharged at a pressure higher than atmospheric pressure through the steam discharge path. In addition, steam heated to 100° C. or more may be brought into contact with the coffee beans under atmospheric pressure. As an apparatus for the treatment, there are given, for example, an autoclave and a superheated steam treatment apparatus.

Conditions for the steam treatment are, in terms of an F0 value, preferably 0.5 min or more, more preferably 1.0 min or more, even more preferably 5.0 min or more, from the viewpoint of the yield of the chlorogenic acid, and are preferably 250 min or less, more preferably 100 min or less, even more preferably 50 min or less, from the viewpoint of a reduction in turbidity. Such F0 value falls within the range of preferably from 0.5 min to 250 min, more preferably from 1.0 min to 100 min, even more preferably from 5.0 min to 50 min. The F0 value is a value calculated by the following equation.

$$F0 \text{ value (min)} = A \times 10^{\frac{(B-121.1)}{10}}$$

In the equation, A represents a treatment time (min), and B represents a treatment temperature (° C.)

The coffee beans after the steam treatment may be cooled or dried (e.g., vacuum-dried or dried with hot air) as required, or may be directly subjected to extraction without cooling or the like.

In addition, in the present invention, degassed coffee beans may be used as the coffee beans from the viewpoint of the yield of the chlorogenic acid. In the case of using degassed ground coffee beans as the coffee beans, ground coffee beans may be subjected to degassing treatment or whole ground coffee beans may be subjected to degassing treatment before being ground.

As a method for the degassing treatment, there is given, for example, a method involving bringing coffee beans into contact with an aqueous solvent. An example of such aqueous solvent is an aqueous solvent to be used for extraction to be described later.

The usage amount of such aqueous solvent is preferably 0.1 part by mass or more, more preferably 0.5 part by mass or more, even more preferably 1 part by mass or more, and preferably 10 parts by mass or less, more preferably 5 parts by mass or less, even more preferably 3 parts by mass or less, with respect to the coffee beans, from the viewpoint of the elimination of air in the coffee beans. The usage amount of such aqueous solvent falls within the range of preferably from 0.1 part by mass to 10 parts by mass, more preferably from 0.5 part by mass to 5 parts by mass, even more preferably from 1 part by mass to 3 parts by mass, with respect to the coffee beans.

A contact time is preferably 1 min or more, more preferably 2 min or more, even more preferably 3 min or more, from the viewpoint of the elimination of air in the coffee beans, and is preferably 120 min or less, more preferably 90 min or less, even more preferably 60 min or less, from the viewpoint of production efficiency. Such contact time falls within the range of preferably from 1 min to 120 min, more preferably from 2 min to 90 min, even more preferably from 3 min to 60 min.

Further, at the time of the contact between the coffee beans and the aqueous solvent, the pressure may be increased or reduced in order to promote degassing.

In the case of a reduced pressure condition, the pressure at the time of such contact is preferably 0.09 MPa or less, more preferably 0.05 MPa or less, even more preferably 0.01 MPa or less, from the viewpoint of the elimination of air in the coffee beans. In addition, in the case of an increased pressure condition, the pressure is preferably 0.11 MPa or more, more preferably 0.15 MPa or more, even more preferably 0.2 MPa or more.

[Extraction]

In the present invention, the coffee beans are subjected to column extraction. When the coffee beans are subjected to batch extraction, turbidity is not sufficiently reduced.

The term "column extraction" as used herein refers to an operation of performing extraction by feeding an aqueous solvent through a column. As a suitable mode, there is given an operation involving supplying the aqueous solvent into the inside of the column, and simultaneously, discharging an extract solution to the outside of the column.

The column extractor is not particularly limited as long as the column extractor comprises, for example, a supply port for hot water and a discharge port for the extract solution. A column extractor comprising the following is suitably used: a supply valve for supplying hot water and a discharge valve for discharging the extract solution, which are arranged in the lower part of the extractor; a shower nozzle for supplying the aqueous solvent, which is arranged in the upper part; and a retainer plate for retaining the coffee beans, which is arranged inside the extractor. The retainer plate is not particularly limited as long as the coffee beans and the extract solution can be separated from each other. Examples thereof may include a mesh and a punched metal. As the shape of the retainer plate, there are given, for example, a flat plate shape, a conical shape, and a pyramidal shape. In addition, the opening size of the retainer plate is not particularly limited as long as the opening size is smaller than the average particle size of the coffee beans, and may be appropriately selected.

In addition, as a method of loading the column extractor with the coffee beans, it is appropriate to put the coffee beans into the column extractor. When two or more kinds of coffee beans are used, the column extractor may be loaded with a mixture of the two or more kinds of coffee beans, or may be loaded with layers of the respective kinds of coffee beans.

The aqueous solvent is used for the extraction, and examples of the aqueous solvent include water, a water-soluble organic solvent, water-soluble organic solvent-containing water, milk, and carbonated water. Examples of the water-soluble organic solvent include an alcohol, a ketone, and an ester. In consideration of use in foods, an alcohol is preferred, and ethanol is more preferred. The concentration of the water-soluble organic solvent in the water-soluble organic solvent-containing water may be appropriately selected.

Of those, as the aqueous solvent, water is preferred. Examples of the water include tap water, natural water, distilled water, and ion-exchanged water. Of those, ion-exchanged water is preferred in terms of taste.

In addition, the pH (20° C.) of the aqueous solvent is generally from 4 to 10, and is preferably from 5 to 7 from the viewpoint of taste and flavor. In order to achieve a desired pH, the pH may be adjusted by adding a pH adjuster into the aqueous solvent. Examples of the pH adjuster include sodium hydrogen bicarbonate, sodium hydrogen carbonate, L-ascorbic acid, and sodium L-ascorbate.

The temperature of the aqueous solvent is preferably 75° C. or more, more preferably 77° C. or more, more preferably 79° C. or more, even more preferably 80° C. or more, from the viewpoint of an increase in recovery rate of the chlorogenic acid, and is preferably 98° C. or less, more preferably 95° C. or less, more preferably 90° C. or less, more preferably 89° C. or less, more preferably 87° C. or less, even more preferably 85° C. or less, from the viewpoint of a reduction in turbidity. The temperature of the aqueous solvent falls within the range of preferably from 75° C. to 98° C., more preferably from 77° C. to 95° C., more preferably from 77° C. to 90° C., more preferably from 79° C. to 89° C., more preferably from 79° C. to 87° C., even more preferably from 80° C. to 85° C.

The aqueous solvent may be supplied from the lower part of the column extractor toward the upper part thereof (upflow), or from the upper part of the column extractor toward the lower part thereof (downflow). In addition, the following may be performed: the aqueous solvent is supplied in a predetermined amount from the lower part of the column extractor and the supply is stopped, and then the aqueous solvent is supplied from the shower nozzle in the upper part, and simultaneously, the extract solution is discharged from the lower part. In this case, the supply amount of the aqueous solvent from the lower part may be appropriately set, and is preferably such an amount that part of the coffee beans in the column extractor can be immersed in the aqueous solvent.

The feeding amount of the aqueous solvent in terms of bed volume (BV) with respect to the mass of the coffee beans is preferably 1 (w/w) or more, more preferably 2 (w/w) or more, even more preferably 3 (w/w) or more, from the viewpoint of an increase in recovery rate of the chlorogenic acid, and is preferably 30 (w/w) or less, more preferably 25 (w/w) or less, even more preferably 20 (w/w) or less, from the viewpoint of a concentration load. Such bed volume (BV) falls within the range of preferably from 1 (w/w) to 30 (w/w), more preferably from 2 (w/w) to 25 (w/w), even more preferably from 3 (w/w) to 20 (w/w).

In addition, the feeding rate of the aqueous solvent is preferably 0.1 [hr$^{-1}$] or more, more preferably 0.3 [hr$^{-1}$] or more, even more preferably 0.5 [hr$^{-1}$] or more, and is preferably 20 [hr$^{-1}$] or less, more preferably 10 [hr$^{-1}$] or less, even more preferably 5 [hr$^{-1}$] or less, in terms of space velocity (SV) with respect to the mass of the coffee beans, from the viewpoint of an increase in recovery rate of the chlorogenic acid. Such space velocity (SV) falls within the range of preferably from 0.1 [hr$^{-1}$] to 20 [hr$^{-1}$], more preferably from 0.3 [hr$^{-1}$] to 10 [hr$^{-1}$], even more preferably from 0.5 [hr$^{-1}$] to 5 [hr$^{-1}$], and may fall within the range of from 0.1 [hr$^{-1}$] to 10 [hr$^{-1}$].

The chlorogenic acid-containing composition of the present invention may be obtained by recovering the extract solution discharged from the column extractor, and may be further subjected to solid-liquid separation usually used in the field of food industry, as required. Examples of the solid-liquid separation include paper filtration, centrifugal separation, and membrane filtration. One kind thereof may be carried out, or two or more kinds thereof may be appropriately carried out in combination.

The chlorogenic acid-containing composition may be in any of various forms, such as a liquid, a slurry, a semisolid, and a solid. The chlorogenic acid-containing composition may be concentrated. As a concentration method, there are given, for example, a normal-pressure concentration method, a reduced-pressure concentration method, and a membrane concentration method. Concentration conditions may be appropriately selected depending on the concentration method. In addition, when the product form of the chlorogenic acid-containing composition is a solid, the chlorogenic acid-containing composition may be dried by a known method, such as spray drying or freeze drying.

The chlorogenic acid-containing composition obtained by the production method of the present invention may have the following features (i) to (iii).

(i) The chlorogenic acid-containing composition may have a turbidity of preferably 150 NTU or less, more preferably 120 NTU or less, more preferably 100 NTU or less, even more preferably 90 NTU or less, when adjusted to a concentration of the chlorogenic acid of 0.3 mass % and a pH of 3. The above-mentioned "turbidity of 150 NTU or less" indicates a standard at which, even when the chlorogenic acid-containing composition is blended into an acidic transparent beverage so as to have a concentration of the chlorogenic acid of 0.3 mass %, the aesthetics of the beverage is hardly impaired. In addition, the above-mentioned "turbidity of 90 NTU or less" indicates a standard at which, even when the chlorogenic acid-containing composition is blended into an acidic transparent beverage so as to have a concentration of the chlorogenic acid of 0.4 mass %, the aesthetics of the beverage is hardly impaired. The term "transparent beverage" as used herein refers to a beverage having an absorbance of 0.06 or less at a wavelength of 660 nm in measurement with a UV-visible spectrophotometer (e.g., UV-1600 (manufactured by Shimadzu Corporation)). The term "turbidity" as used herein refers to a value measured by a method described in Examples. In addition, the term "NTU" refers to a measurement unit of a formazin turbidity using a formazin turbidity standard.

(ii) The chlorogenic acid-containing composition may contain preferably 10 mass % to 80 mass %, more preferably 25 mass % to 75 mass %, even more preferably 30 mass % to 60 mass % of the chlorogenic acid in a solid content, from the viewpoint of taste and flavor. The term "solid content" as used herein refers to a residue obtained by drying a sample in an electric thermostat dryer at 105° C. for 3 hours to remove volatile substances.

(iii) The chlorogenic acid-containing composition may have a yield of the chlorogenic acid, calculated by a method described in Examples to be described later, of preferably 50% or more, more preferably 60% or more, more preferably 70% or more, even more preferably 80% or more.

The present invention further discloses the following production method regarding the above-mentioned embodiment.

<1>

A method of producing a chlorogenic acid-containing composition, comprising a step of subjecting coffee beans to column extraction using an aqueous solvent, wherein the coffee beans comprise at least one selected from the group consisting of green coffee beans, decaffeinated green coffee beans, roasted coffee beans having an L value of 40 or more, and decaffeinated roasted coffee beans having an L value of 25 or more, and comprise at least one selected from the group consisting of unground coffee beans and ground coffee beans having an average particle size of 2 mm or more.

<2>

The method of producing a chlorogenic acid-containing composition according to the above-mentioned item <1>, wherein the chlorogenic acid comprises preferably at least one selected from the group consisting of 3-caffeoylquinic acid, 4-caffeoylquinic acid, 5-caffeoylquinic acid, 3-feruloylquinic acid, 4-feruloylquinic acid, and 5-feruloylquinic acid, more preferably all of the six kinds.

<3>

The method of producing a chlorogenic acid-containing composition according to the above-mentioned item <1> or <2>, wherein a bean species of the coffee beans comprises preferably at least one selected from the group consisting of *Arabica, Robusta, Liberica*, and *Arabusta*.

<4>

The method of producing a chlorogenic acid-containing composition according to any one of the above-mentioned items <1> to <3>, wherein decaffeination treatment comprises preferably a Swiss Water method, a supercritical carbon dioxide extraction method, or an organic solvent extraction method, more preferably a Swiss Water method or a supercritical carbon dioxide extraction method.

<5>

The method of producing a chlorogenic acid-containing composition according to any one of the above-mentioned items <1> to <4>, wherein the L value of the roasted coffee beans is preferably 40 or more and less than 65, more preferably 45 or more and less than 65, more preferably 53 or more and less than 65, more preferably from 55 to 60, even more preferably from 55 to 58.

<6>

The method of producing a chlorogenic acid-containing composition according to any one of the above-mentioned items <1> to <4>, wherein the L value of the decaffeinated roasted coffee beans is preferably 25 or more and less than 50, more preferably from 30 to 45, even more preferably from 33 to 40.

<7>

The method of producing a chlorogenic acid-containing composition according to any one of the above-mentioned items <1> to <6>, wherein the coffee beans preferably comprise ground coffee beans, and the ground coffee beans have an average particle size of preferably from 2.5 mm to 7.5 mm, more preferably from 3.5 mm to 7.0 mm, more

<8>

The method of producing a chlorogenic acid-containing composition according to any one of the above-mentioned items <1> to <7>, wherein the coffee beans preferably comprise green coffee beans or decaffeinated green coffee beans, and comprise unground coffee beans.

<9>

The method of producing a chlorogenic acid-containing composition according to any one of the above-mentioned items <1> to <8>, wherein the coffee beans preferably comprise coffee beans subjected to steam treatment.

<10>

The method of producing a chlorogenic acid-containing composition according to the above-mentioned item <9>, wherein conditions for the steam treatment are, in terms of an F0 value, preferably 0.5 min or more, more preferably 1.0 min or more, even more preferably 5.0 min or more, and are preferably 250 min or less, more preferably 100 min or less, even more preferably 50 min.

<11>

The method of producing a chlorogenic acid-containing composition according to the above-mentioned item <9> or <10>, wherein conditions for the steam treatment are, in terms of an F0 value, preferably from 0.5 min to 250 min, more preferably from 1.0 min to 100 min, even more preferably from 5.0 min to 50 min.

<12>

The method of producing a chlorogenic acid-containing composition according to any one of the above-mentioned items <1> to <11>, wherein the coffee beans preferably comprise coffee beans subjected to degassing treatment.

<13>

The method of producing a chlorogenic acid-containing composition according to any one of the above-mentioned items <1> to <12>, wherein the aqueous solvent comprises preferably at least one selected from the group consisting of water, a water-soluble organic solvent, water-soluble organic solvent-containing water, milk, and carbonated water, more preferably water.

<14>

The method of producing a chlorogenic acid-containing composition according to the above-mentioned item <13>, wherein the water-soluble organic solvent comprises preferably an alcohol, a ketone, or a nester, more preferably an alcohol, even more preferably ethanol.

<15>

The method of producing a chlorogenic acid-containing composition according to any one of the above-mentioned items <1> to <14>, wherein the aqueous solvent has a pH of preferably from 4 to 10, more preferably from 5 to 7.

<16>

The method of producing a chlorogenic acid-containing composition according to any one of the above-mentioned items <1> to <15>, wherein the aqueous solvent has a temperature of preferably from 75° C. to 98° C., more preferably from 77° C. to 95° C., more preferably from 77° C. to 90° C., more preferably from 79° C. to 89° C., more preferably from 79° C. to 87° C., even more preferably from 80° C. to 85° C.

<17>

The method of producing a chlorogenic acid-containing composition according to any one of the above-mentioned items <1> to <16>, wherein a feeding direction of the aqueous solvent is preferably from a lower part of a column extractor toward an upper part thereof (upflow), or from an upper part of a column extractor toward a lower part thereof (downflow).

<18>

The method of producing a chlorogenic acid-containing composition according to any one of the above-mentioned items <1> to <17>, wherein a feeding amount of the aqueous solvent is preferably from 1 (w/w) to 30 (w/w), more preferably from 2 (w/w) to 25 (w/w), even more preferably from 3 (w/w) to 20 (w/w), in terms of bed volume (BV) with respect to a mass of the coffee beans.

<19>

The method of producing a chlorogenic acid-containing composition according to any one of the above-mentioned items <1> to <18>, wherein a feeding rate of the aqueous solvent in terms of space velocity (SV) with respect to a mass of the coffee beans is preferably from 0.1 [hr$^-$] to 20 [hr$^{-1}$], more preferably from 0.3 [hr$^{-1}$] to 10 [hr$^{-1}$], even more preferably from 0.5 [hr$^{-1}$] to 5 [hr$^{-1}$], and may be from 0.1 [hr$^{-1}$] to 10 [hr$^{-1}$].

<20>

The method of producing a chlorogenic acid-containing composition according to any one of the above-mentioned items <1> to <19>, preferably further comprising a step of subjecting an extract solution discharged from a column extractor to solid-liquid separation.

<21>

The method of producing a chlorogenic acid-containing composition according to the above-mentioned item <20>, wherein the solid-liquid separation preferably comprises one kind or two or more kinds selected from the group consisting of paper filtration, centrifugal separation, and membrane filtration.

<22>

The method of producing a chlorogenic acid-containing composition according to any one of the above-mentioned items <1> to <21>, wherein the chlorogenic acid-containing composition is preferably in a liquid, slurry, semisolid, or solid form, and may be concentrated.

<23>

The method of producing a chlorogenic acid-containing composition according to any one of the above-mentioned items <1> to <22>, wherein the chlorogenic acid-containing composition has a turbidity of preferably 150 NTU or less, more preferably 120 NTU or less, more preferably 100 NTU or less, even more preferably 90 NTU or less, when adjusted to a concentration of the chlorogenic acid of 0.3 mass % and a pH of 3.

<24>

The method of producing a chlorogenic acid-containing composition according to any one of the above-mentioned items <1> to <23>, wherein the chlorogenic acid-containing composition has a content of the chlorogenic acid in a solid content of preferably from 10 mass % to 80 mass %, more preferably from 25 mass % to 75 mass %, even more preferably from 30 mass % to 60 mass %.

<25>

The method of producing a chlorogenic acid-containing composition according to any one of the above-mentioned items <1> to <24>, wherein the chlorogenic acid-containing composition has a yield of the chlorogenic acid of preferably 50% or more, more preferably 60% or more, more preferably 70% or more, even more preferably 80% or more.

EXAMPLES

1. Analysis of Chlorogenic Acid (CGA) and Caffeine (Caf) (Analyzer)

An UPLC (manufactured by Nihon Waters K.K.) was used. The model numbers of component units in the analyzer are as follows:
Apparatus: Waters ACQUITY UPLC
Column: ACQUITY UPLC TM C18, 2.1×100 nm, 1.7 μm
Detector: photodiode array detector (PDA)
(Analysis Conditions)
Sample injection volume: 10 μL
Flow rate: 1.0 mL/min
Ultraviolet absorption spectrophotometer detection wavelengths: 325 nm (chlorogenic acid) and 270 nm (caffeine)
Eluent A: A solution of acetonitrile diluted with water to an acetonitrile concentration of 5 (V/V) %, the solution containing 0.05 M acetic acid, 0.1 mM 1-hydroxyethane-1,1-diphosphonic acid, and 10 mM sodium acetate
Eluent B: Acetonitrile
Concentration Gradient Conditions (vol %)

| Time | Eluent A | Eluent B |
|---|---|---|
| 0.0 min | 100% | 0% |
| 2.5 min | 100% | 0% |
| 3.5 min | 95% | 5% |
| 5.0 min | 95% | 5% |
| 6.0 min | 92% | 8% |
| 16.0 min | 92% | 8% |
| 16.5 min | 10% | 90% |
| 19.0 min | 100% | 0% |
| 22.0 min | 100% | 0% |

(1) Retention Time of Chlorogenic Acid (CGA)
3-Caffeoylquinic acid (3-CQA): 1.3 min
5-Caffeoylquinic acid (5-CQA): 2.1 min
4-Caffeoylquinic acid (4-CQA): 2.9 min
3-Feruloylquinic acid (3-FQA): 3.3 min
5-Feruloylquinic acid (5-FQA): 5.0 min
4-Feruloylquinic acid (4-FQA): 5.4 min 5-CQA was used as a standard substance to determine the content (mass %) of the chlorogenic acid based on the area % determined in the foregoing.

(2) Retention Time of Caffeine (Caf)
Caffeine: 4.8 min

Reagent caffeine was used as a standard substance to determine the content (mass %) of caffeine based on the area % determined in the foregoing.

2. Measurement of L Value of Roasted Coffee Beans

A sample ground to an average particle size of 0.3 mm was subjected to measurement using a colorimeter (manufactured by Nippon Denshoku Industries Co., Ltd., Spectrophotometer SE2000).

3. Measurement of Average Particle Size of Ground Coffee Beans

Ten ground coffee beans were randomly taken, each of the beans was measured for its long diameter, short diameter, and intermediate diameter with a vernier caliper, and the average of the measured values was defined as an average particle size. As used herein, the term "long diameter" refers to the length of the longest portion in an observation surface of a ground coffee bean, the term "short diameter" refers to the length of the longest portion in the direction perpendicular to the long diameter, and the term "intermediate diameter" refers to the length of the longest portion in the vertical direction of the observation surface. However, when such value was 2 mm or less, the "average particle size" was determined as a particle diameter corresponding to 500 ($d_{50}$) in a cumulative particle size distribution curve on a volume basis obtained by dry measurement with a laser diffraction/scattering particle size distribution analyzer (LS13 320, manufactured by Beckman Coulter) utilizing the dependence of a diffracted/scattered light intensity pattern on the size of a particle.

4. Analysis of Turbidity

A chlorogenic acid-containing composition was adjusted to a concentration of the chlorogenic acid of 0.3 mass % and a pH of 3 through the use of water, or as required, at least one selected from the group consisting of hydrochloric acid and an aqueous sodium hydroxide solution. The resultant adjusted solution was subjected to measurement at 25° C. using a turbidimeter (TN-100, manufactured by Eutech Instruments Pte Ltd.).

5. Calculation of Chlorogenic Acid (CGA) Yield

The yield of a chlorogenic acid-containing composition was calculated by the following equation. In the following equation, coffee beans refer to unground green robusta coffee beans used in each Example. In addition, the content of the chlorogenic acid in the coffee beans refers to a value calculated as the amount of the chlorogenic acid in a solution recovered by grinding the coffee beans to an average particle size of 1.4 mm, charging the resultant into a column, and then feeding hot water at 95° C. under the conditions of a feeding rate (SV) of 5 [$hr^{-1}$] and a bed volume (BV) with respect to the mass of the coffee beans of 10 (w/w).

$$\text{CGA yield (\%)} = (X \times Y/100)/(W \times Z/100) \times 100$$

In the equation, X represents the mass (g) of the chlorogenic acid-containing composition, Y represents the content (mass %) of the chlorogenic acid in the chlorogenic acid-containing composition, W represents the mass (g) of the coffee beans, and Z represents the content (mass %) of the chlorogenic acid in the coffee beans.

Example 1

45 g of unground green robusta coffee beans were charged into a column having a volume of 208 cm³. Next, 3 parts by mass of hot water at 70° C. was supplied to the column from a shower nozzle in an upper part of the column at a feeding rate of SV=2 [$hr^{-1}$] to charge the column. Next, hot water at 70° C. was supplied from the shower nozzle in the upper part under the conditions of a feeding rate (SV) of 2 [$hr^{-1}$] and a bed volume (BV) of 15 (w/w), and simultaneously, a discharge valve in a lower part of the column was opened to continuously take out a "chlorogenic acid-containing composition". The resultant chlorogenic acid-containing composition was analyzed. The results are shown in Table 1.

Example 2

A chlorogenic acid-containing composition was obtained in the same manner as in Example 1 except that the temperature of the hot water was changed to 75° C. The resultant chlorogenic acid-containing composition was analyzed. The results are shown in Table 1.

Example 3

A chlorogenic acid-containing composition was obtained in the same manner as in Example 1 except that the temperature of the hot water was changed to 80° C. The resultant chlorogenic acid-containing composition was analyzed. The results are shown in Table 1.

Example 4

A chlorogenic acid-containing composition was obtained in the same manner as in Example 1 except that the temperature of the hot water was changed to 85° C. The resultant chlorogenic acid-containing composition was analyzed. The results are shown in Table 1.

Example 5

A chlorogenic acid-containing composition was obtained in the same manner as in Example 1 except that the temperature of the hot water was changed to 90° C. The resultant chlorogenic acid-containing composition was analyzed. The results are shown in Table 1.

Example 6

A chlorogenic acid-containing composition was obtained in the same manner as in Example 1 except that the temperature of the hot water was changed to 95° C. The resultant chlorogenic acid-containing composition was analyzed. The results are shown in Table 1.

Example 7

A chlorogenic acid-containing composition was obtained in the same manner as in Example 1 except that the temperature of the hot water was changed to 98° C. The resultant chlorogenic acid-containing composition was analyzed. The results are shown in Table 1.

Example 8

A chlorogenic acid-containing composition was obtained in the same manner as in Example 4 except that unground decaffeinated green robusta coffee beans (L value: 44; produced by supercritical treatment; manufactured by Atlantic Coffee Solutions; Vietnam Robusta G2 decafe) were used. The resultant chlorogenic acid-containing composition was analyzed. The results are shown in Table 1.

Example 9

Unground green robusta coffee beans were ground and classified to provide ground green coffee beans having an average particle size of 4.2 mm. Next, with the use of 45 g of the ground green coffee beans, a chlorogenic acid-containing composition was obtained in the same manner as in Example 4. The resultant chlorogenic acid-containing composition was analyzed. The results are shown in Table 1.

Example 10

Unground green robusta coffee beans were ground and classified to provide ground green coffee beans having an average particle size of 6.1 mm. Next, with the use of 45 g of the ground green coffee beans, a chlorogenic acid-containing composition was obtained in the same manner as in Example 4. The resultant chlorogenic acid-containing composition was analyzed. The results are shown in Table 1.

Example 11

A chlorogenic acid-containing composition was obtained in the same manner as in Example 4 except that roasted coffee beans (L value: 50) obtained by roasting unground green robusta coffee beans were used. The resultant chlorogenic acid-containing composition was analyzed. The results are shown in Table 1.

Comparative Example 1

90 g of unground green robusta coffee beans were put into a 2 L four-necked flask. Next, 1,350 g of hot water at 75° C. was added to the green coffee beans in the four-necked flask, and the contents were stirred for 4 hours, followed by filtration through a mesh, to provide a "chlorogenic acid-containing composition". The resultant chlorogenic acid-containing composition was analyzed. The results are shown in Table 1.

Comparative Example 2

90 g of unground green robusta coffee beans were put into a 2 L four-necked flask. Next, 1,350 g of hot water at 80° C. was added to the green coffee beans in the four-necked flask, and the contents were stirred for 4 hours, followed by filtration through a mesh, to provide a "chlorogenic acid-containing composition". The resultant chlorogenic acid-containing composition was analyzed. The results are shown in Table 1.

Comparative Example 3

90 g of unground green robusta coffee beans were put into a 2 L four-necked flask. Next, 1,350 g of hot water at 95° C. was added to the green coffee beans in the four-necked flask, and the contents were stirred for 4 hours, followed by filtration through a mesh, to provide a "chlorogenic acid-containing composition". The resultant chlorogenic acid-containing composition was analyzed. The results are shown in Table 1.

Comparative Example 4

Unground green robusta coffee beans were ground with a cutter mill, and classified using a sieve having a mesh size of 1 mm and a sieve having a mesh size of 1.7 mm to provide ground green coffee beans having an average particle size of 1.4 mm. Next, with the use of 45 g of the ground green coffee beans, a chlorogenic acid-containing composition was obtained in the same manner as in Example 4. The resultant chlorogenic acid-containing composition was analyzed. The results are shown in Table 1.

Comparative Example 5

A chlorogenic acid-containing composition was obtained in the same manner as in Example 4 except that roasted coffee beans (L value: 35) obtained by roasting unground green robusta coffee beans were used. The resultant chlorogenic acid-containing composition was analyzed. The results are shown in Table 1.

TABLE 1

|  |  | Example 1 | Example 2 | Example 3 | Example 4 | Example 5 | Example 6 | Example 7 | Example 8 |
|---|---|---|---|---|---|---|---|---|---|
| Coffee beans | Green beans or roasted beans (L value) | Green beans | Green beans | Green beans | Green beans | Green beans | Green beans | Green beans | Decaffenated green beans |
|  | Particle size (average particle size) | Unground | Unground | Unground | Unground | Unground | Unground | Unground | Unground |
|  | Steam treatment (conditions) | Absent | Absent | Absent | Absent | Absent | Absent | Absent | Absent |
| Extraction | Mode | Column | Column | Column | Column | Column | Column | Column | Column |
|  | Temperature | 70 | 75 | 80 | 85 | 90 | 95 | 98 | 85 |
| Analysis results | Turbidity (NTU) | 28 | 20 | 18 | 26 | 63 | 93 | 146 | 55 |
|  | CGA yield (%) | 49 | 50 | 72 | 75 | 82 | 81 | 85 | 61 |

|  |  | Example 9 | Example 10 | Example 11 | Comparative Example 1 | Comparative Example 2 | Comparative Example 3 | Comparative Example 4 | Comparative Example 5 |
|---|---|---|---|---|---|---|---|---|---|
| Coffee beans | Green beans or roasted beans (L value) | Green beans | Green beans | Roasted beans L50 | Green beans | Green beans | Green beans | Green beans | Roasted beans L35 |
|  | Particle size (average particle size) | 4.2 mm | 6.1 mm | Unground | Unground | Unground | Unground | 1.4 mm | Unground |
|  | Steam treatment (conditions) | Absent | Absent | Absent | Absent | Absent | Absent | Absent | Absent |
| Extraction | Mode | Column | Column | Column | Batch | Batch | Batch | Column | Column |
|  | Temperature | 85 | 85 | 85 | 75 | 80 | 95 | 85 | 85 |
| Analysis results | Turbidity (NTU) | 108 | 63 | 106 | 280 | 263 | 430 | 1,000 | 421 |
|  | CGA yield (%) | 86 | 83 | 73 | 67 | 74 | 77 | 88 | 48 |

Example 12

Superheated steam was supplied to unground green robusta coffee beans at a rate of 2.8 w/min from a lower part of a column, and continuously discharged through an upper part of the column. In this manner, steam treatment was performed at 108° C. for 10 minutes. Next, a chlorogenic acid-containing composition was obtained in the same manner as in Example 4 except that the green coffee beans after the steam treatment were used. The resultant chlorogenic acid-containing composition was analyzed. The results are shown in Table 2 together with the results of Example 4.

Example 13

Superheated steam was supplied to unground green robusta coffee beans at a rate of 2.8 w/min from a lower part of a column, and continuously discharged through an upper part of the column. In this manner, steam treatment was performed at 118° C. for 10 minutes. Next, a chlorogenic acid-containing composition was obtained in the same manner as in Example 4 except that the green coffee beans after the steam treatment were used. The resultant chlorogenic acid-containing composition was analyzed. The results are shown in Table 2 together with the results of Example 4.

Example 14

Superheated steam was supplied to unground green robusta coffee beans at a rate of 2.8 w/min from a lower part of a column, and continuously subjected to discharging treatment through an upper part of the column. In this manner, steam treatment was performed at 135° C. for 10 minutes. Next, a chlorogenic acid-containing composition was obtained in the same manner as in Example 4 except that the green coffee beans after the steam treatment were used. The resultant chlorogenic acid-containing composition was analyzed. The results are shown in Table 2 together with the results of Example 4.

TABLE 2

|  |  | Example 12 | Example 13 | Example 14 | Example 4 |
|---|---|---|---|---|---|
| Coffee beans | Green beans or roasted beans (L value) | Green beans | Green beans | Green beans | Green beans |
|  | Particle size (average particle size) | Unground | Unground | Unground | Unground |
|  | Steam treatment (conditions) | 108° C. · 10 min | 118° C. · 10 min | 135° C. · 10 min | Absent |

TABLE 2-continued

|  |  | Example 12 | Example 13 | Example 14 | Example 4 |
|---|---|---|---|---|---|
| Steam treatment | F0 value | 0.78 | 7.76 | 123.03 | 0 |
| Extraction | Mode | Column | Column | Column | Column |
|  | Temperature | 85 | 85 | 85 | 85 |
| Analysis results | Turbidity (NTU) | 45 | 84 | 93 | 26 |
|  | CGA yield (%) | 76 | 78 | 84 | 75 |

Example 15

Unground green robusta coffee beans were subjected to degassing treatment involving contact with 2 parts by mass of water at 5° C. under a reduced pressure of 0.003 MPa for 5 min. Next, a chlorogenic acid-containing composition was obtained in the same manner as in Example 2 except that the green coffee beans after the degassing treatment were used. The resultant chlorogenic acid-containing composition was analyzed. The results are shown in Table 3 together with the results of Example 2.

TABLE 3

|  |  | Example 15 | Example 2 |
|---|---|---|---|
| Coffee beans | Green beans or roasted beans (L value) | Green beans | Green beans |
|  | Particle size (average particle size) | Unground | Unground |
|  | Steam treatment (conditions) | Absent | Absent |
|  | Degassing treatment | Present | Absent |
| Extraction | Mode | Column | Column |
|  | Temperature | 75 | 75 |
| Analysis results | Turbidity (NTU) | 27 | 20 |
|  | CGA yield (%) | 63 | 50 |

It is apparent from Tables 1 to 3 that a chlorogenic acid-containing composition that hardly causes turbidity even when the concentration of the chlorogenic acid is diluted to an optimum concentration as a beverage to provide an acidic beverage is obtained by: using, as coffee beans, at least one selected from the group consisting of green coffee beans, decaffeinated green coffee beans, roasted coffee beans having an L value of 40 or more, and decaffeinated roasted coffee beans having an L value of 25 or more, the coffee beans being at least one selected from the group consisting of unground coffee beans and ground coffee beans having an average particle size of 2 mm or more; and subjecting the coffee beans to column extraction using an aqueous solvent.

The invention claimed is:

1. A method of producing a chlorogenic acid-containing composition, comprising a step of subjecting coffee beans to column extraction using water at from 70° C. to 98° C., wherein the coffee beans are decaffeinated roasted coffee beans having an L value of 30 or more and less than 50, and comprise at least one selected from the group consisting of unground coffee beans and ground coffee beans having an average particle size of 4.2 mm or more.

2. The method of producing a chlorogenic acid-containing composition according to claim 1, wherein an extraction temperature in the step of subjecting coffee beans to column extraction is from 75° C. to 98° C.

3. The method of producing a chlorogenic acid-containing composition according to claim 1, wherein the average particle size of the ground coffee beans is from 4.5 mm to 7.5 mm.

4. The method of producing a chlorogenic acid-containing composition according to claim 1, wherein the coffee beans comprise coffee beans subjected to steam treatment.

5. The method of producing a chlorogenic acid-containing composition according to claim 4, wherein conditions for the steam treatment are from 0.5 min to 250 min in terms of an F0 value.

6. The method of producing a chlorogenic acid-containing composition according to claim 1, wherein a supply amount of the water is from 1 (w/w) to 30 (w/w) in terms of bed volume with respect to a mass of the coffee beans.

7. The method of producing a chlorogenic acid-containing composition according to claim 1, wherein a supply rate of the water is from 0.1 [hr$^{-1}$] to 20 [hr$^{-1}$] in terms of feeding rate (SV).

8. The method of producing a chlorogenic acid-containing composition according to claim 1, wherein the coffee beans comprise coffee beans subjected to degassing treatment.

9. The method of producing a chlorogenic acid-containing composition according to claim 1, wherein the water has a pH of from 4 to 10.

10. The method of producing a chlorogenic acid-containing composition according to claim 1, wherein a feeding rate of the water is 0.1 [hr$^{-1}$] to 10 [hr$^{-1}$] in terms of space velocity (SV) with respect to a mass of the coffee beans.

11. The method of producing a chlorogenic acid-containing composition according to claim 1, further comprising a step of subjecting an extract solution discharged from a column extractor to solid-liquid separation.

12. A method of producing a chlorogenic acid-containing composition, comprising a step of subjecting coffee beans to column extraction using water at from 70° C. to 98° C.,
    wherein the coffee beans are at least one selected from the group consisting of green coffee beans and decaffeinated green coffee beans, and comprise at least one selected from the group consisting of unground coffee beans and ground coffee beans having an average particle size of 4.2 mm or more, and
    wherein the composition possesses a turbidity of 150 NTU or less when adjusted to a concentration of the chlorogenic acid of 0.3 mass % and a pH of 3.

13. A method of producing a chlorogenic acid-containing composition, comprising a step of subjecting coffee beans to column extraction using water at from 70° C. to 98° C.,
    wherein the coffee beans are roasted coffee beans having an L value of 45 or more and less than 65, and comprise at least one selected from the group consisting of unground coffee beans and ground coffee beans having an average particle size of 4.2 mm or more, and
    wherein the composition possesses a turbidity of 150 NTU or less when adjusted to a concentration of the chlorogenic acid of 0.3 mass % and a pH of 3.

* * * * *